(12) United States Patent
Honda et al.

(10) Patent No.: US 8,445,221 B2
(45) Date of Patent: May 21, 2013

(54) MODIFIED GLUCOSE DEHYDROGENASE GENE

(75) Inventors: Michinari Honda, Hiroshima (JP); Ryo Takenaka, Hiroshima (JP); Fuminao Kobayashi, Hiroshima (JP)

(73) Assignee: Ikeda Food Research Co., Ltd., Hiroshima (JP)

( * ) Notice: Subject to any disclaimer, the term of this patent is extended or adjusted under 35 U.S.C. 154(b) by 240 days.

(21) Appl. No.: 12/810,213

(22) PCT Filed: Dec. 26, 2008

(86) PCT No.: PCT/JP2008/073689
§ 371 (c)(1),
(2), (4) Date: Aug. 2, 2010

(87) PCT Pub. No.: WO2009/084616
PCT Pub. Date: Jul. 9, 2009

(65) Prior Publication Data
US 2010/0323378 A1 Dec. 23, 2010

(30) Foreign Application Priority Data

Dec. 28, 2007 (JP) ................................. 2007-340477

(51) Int. Cl.
*C12Q 1/54* (2006.01)
*C12N 9/00* (2006.01)
*C12N 9/02* (2006.01)
*C12N 1/20* (2006.01)
*C07H 21/04* (2006.01)

(52) U.S. Cl.
USPC .......... 435/14; 435/183; 435/189; 435/252.3; 435/320.1

(58) Field of Classification Search
None
See application file for complete search history.

(56) References Cited

FOREIGN PATENT DOCUMENTS

| EP | 1 584 675 | 10/2005 |
|----|-----------|---------|
| EP | 1 739 174 | 1/2007 |
| EP | 1 860 183 | 11/2007 |
| EP | 1 862 543 | 12/2007 |
| EP | 2 022 850 | 2/2009 |
| WO | 2004/058958 | 7/2004 |
| WO | 2006/101239 | 9/2006 |
| WO | 2007/116710 | 10/2007 |
| WO | 2007/139013 | 12/2007 |

OTHER PUBLICATIONS

Wong et al. J Mol Biol. Jan. 27, 2006;355(4):858-71. Epub Nov. 17, 2005.*
Chica et al. Curr Opin Biotechnol. Aug. 2005;16(4):378-84.*
Sen et al. Appl Biochem Biotechnol. Dec. 2007;143(3):212-23.*
Supplementary European Search Report issued Dec. 22, 2010 in corresponding European Application No. EP 08 86 6874.
Igarashi, Satoshi, et al., "Engineering PQQ glucose dehydrogenase with improved substrate specificity Site-directed mutagenesis studies on the active center of PQQ glucose dehydrogenase", Biomolecular Engineering, vol. 21, 2004, pp. 81-89.

* cited by examiner

*Primary Examiner* — Christian Fronda
(74) *Attorney, Agent, or Firm* — Wenderoth, Lind & Ponack, L.L.P.

(57) ABSTRACT

[Object] To provide an FAD-conjugated glucose dehydrogenase having a higher specificity for glucose.
[Means for Resolution] A modified glucose dehydrogenase (GLD) which includes a substitution of at least one amino acid residue selected from the group consisting of amino acid residues at positions 37, 69, 72, 73, 76, 78, 102, 217, 228, 240, 356, 407, 424, 437, 527, and 530 in an amino acid sequence of a wild-type FAD-conjugated glucose dehydrogenase (GLD) represented by SEQ ID NO: 1, and has a decreased ratio of activity for xylose/activity for glucose as compared with the wild-type GLD; a polynucleotide encoding the modified GLD; a recombinant vector containing the polynucleotide; a transformed cell produced by using the recombinant vector; etc.

22 Claims, 1 Drawing Sheet

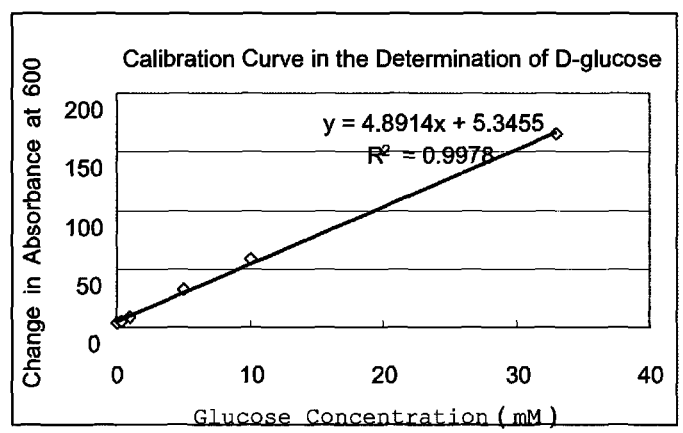

SEQUENCE LISTING

```
<160> NUMBER OF SEQ ID NOS: 34

<210> SEQ ID NO 1
<211> LENGTH: 592
<212> TYPE: PRT
<213> ORGANISM: Aspergillus terreus
<220> FEATURE:
<221> NAME/KEY: SIGNAL
<222> LOCATION: (1)..(19)
```

<400> SEQUENCE: 1

```
Met Leu Gly Lys Leu Ser Phe Leu Ser Ala Leu Ser Leu Ala Val Ala
1               5                   10                  15

Ala Pro Leu Ser Asn Ser Thr Ser Ala Lys Tyr Asp Tyr Ile Val Ile
            20                  25                  30

Gly Gly Gly Thr Ser Gly Leu Ala Val Ala Asn Arg Leu Ser Glu Asp
        35                  40                  45

Pro Asn Val Asn Val Leu Ile Leu Glu Ala Gly Gly Ser Val Trp Asn
50                  55                  60

Asn Pro Asn Val Thr Asn Val Asp Gly Tyr Gly Leu Ala Phe Gly Ser
65                  70                  75                  80

Asp Ile Asp Trp Gln Tyr Gln Ser Val Asn Gln Pro Tyr Gly Gly Asn
                85                  90                  95

Leu Ser Gln Val Leu Arg Ala Gly Lys Ala Leu Gly Gly Thr Ser Thr
            100                 105                 110

Ile Asn Gly Met Ala Tyr Thr Arg Ala Glu Asp Val Gln Ile Asp Ala
        115                 120                 125

Trp Glu Thr Ile Gly Asn Thr Gly Trp Thr Trp Lys Asn Leu Phe Pro
130                 135                 140

Tyr Tyr Arg Lys Ser Glu Asn Phe Thr Val Pro Thr Lys Ser Gln Thr
145                 150                 155                 160

Ser Leu Gly Ala Ser Tyr Glu Ala Gly Ala His Gly His Glu Gly Pro
                165                 170                 175

Leu Asp Val Ala Phe Thr Gln Ile Glu Ser Asn Asn Leu Thr Thr Tyr
            180                 185                 190

Leu Asn Arg Thr Phe Gln Gly Met Gly Leu Pro Trp Thr Glu Asp Val
        195                 200                 205

Asn Gly Gly Lys Met Arg Gly Phe Asn Leu Tyr Pro Ser Thr Val Asn
210                 215                 220

Leu Glu Glu Tyr Val Arg Glu Asp Ala Ala Arg Ala Tyr Tyr Trp Pro
225                 230                 235                 240

Tyr Lys Ser Arg Pro Asn Leu His Val Leu Leu Asn Thr Phe Ala Asn
                245                 250                 255

Arg Ile Val Trp Asp Gly Glu Ala His Asp Gly His Ile Thr Ala Ser
            260                 265                 270

Gly Val Glu Ile Thr Ser Arg Asn Gly Thr Val Arg Val Ile Asn Ala
        275                 280                 285

Glu Lys Glu Val Ile Val Ser Ala Gly Ala Leu Lys Ser Pro Ala Ile
290                 295                 300

Leu Glu Leu Ser Gly Ile Gly Asn Pro Ser Val Leu Asp Lys His Asn
305                 310                 315                 320

Ile Pro Val Lys Val Asn Leu Pro Thr Val Gly Glu Asn Leu Gln Asp
                325                 330                 335

Gln Val Asn Ser His Met Asp Ala Ser Gly Asn Thr Ser Ile Ser Gly
            340                 345                 350

Thr Lys Ala Val Ser Tyr Pro Asp Val Tyr Asp Val Phe Gly Asp Glu
        355                 360                 365

Ala Glu Ser Val Ala Lys Gln Ile Arg Ala Asn Leu Lys Gln Tyr Ala
370                 375                 380

Ala Asp Thr Ala Lys Ala Asn Gly Asn Ile Met Lys Ala Ala Asp Leu
385                 390                 395                 400

Glu Arg Leu Phe Glu Val Gln Tyr Asp Leu Ile Phe Lys Gly Arg Val
                405                 410                 415
```

Pro Ile Ala Glu Val Leu Asn Tyr Pro Gly Ser Ala Thr Ser Val Phe
            420                 425                 430

Ala Glu Phe Trp Ala Leu Leu Pro Phe Ala Arg Gly Ser Val His Ile
        435                 440                 445

Gly Ser Ser Asn Pro Ala Glu Phe Pro Val Ile Asn Pro Asn Tyr Phe
    450                 455                 460

Met Leu Asp Trp Asp Ala Lys Ser Tyr Val Ala Val Ala Lys Tyr Ile
465                 470                 475                 480

Arg Arg Ser Phe Glu Ser Tyr Pro Leu Ser Ser Ile Val Lys Glu Ser
            485                 490                 495

Thr Pro Gly Tyr Asp Val Ile Pro Arg Asn Ala Ser Glu Gln Ser Trp
        500                 505                 510

Lys Glu Trp Val Phe Asp Lys Asn Tyr Arg Ser Asn Phe His Pro Val
    515                 520                 525

Gly Thr Ala Ala Met Met Pro Arg Glu Ile Gly Gly Val Val Asp Glu
530                 535                 540

Arg Leu Asn Val Tyr Gly Thr Thr Asn Val Arg Val Val Asp Ala Ser
545                 550                 555                 560

Val Leu Pro Phe Gln Val Cys Gly His Leu Val Ser Thr Leu Tyr Ala
            565                 570                 575

Val Ala Glu Arg Ala Ala Asp Leu Ile Lys Ala Asp Ala Gly Arg Arg
        580                 585                 590

<210> SEQ ID NO 2
<211> LENGTH: 1779
<212> TYPE: DNA
<213> ORGANISM: Aspergillus terreus
<220> FEATURE:
<221> NAME/KEY: sig_peptide
<222> LOCATION: (1)..(57)

<400> SEQUENCE: 2

| | |
|---|---|
| atgttgggaa agctctcctt cctcagtgcc ctgtccctgg cagtggcggc accttttgtcc | 60 |
| aactccacgt ccgccaaata tgattatatc gttattggag gcggtactag cggttttggcc | 120 |
| gtcgcaaacc gtctatcgga ggatccaaac gtgaacgtac tcattctgga ggccggtggc | 180 |
| tcggtctgga caatcccaa tgtcacaaac gtggatggct acgggcttgc ttttgggtct | 240 |
| gacattgact ggcaatacca gtccgtcaac cagccatatg gaggcaacct tagtcaagtg | 300 |
| cttcgtgccg gcaaggccct tggtggtact agtactatca atggcatggc ctatacgcgc | 360 |
| gccgaggatg tccagatcga cgcctgggaa accattggca cacaggatg gacgtggaag | 420 |
| aatctgttcc cttactatcg gaagagcgag aactttactg tccctaccaa atcgcagacc | 480 |
| tctcttggag cgtcgtatga agctggagcc cacggccacg agggtcccct tgacgttgcc | 540 |
| ttcactcaga tcgagtcgaa caacctgacc acttacctca accgtacctt ccagggcatg | 600 |
| ggactcccat ggacggagga cgtcaatggc ggaaagatgc gcggctttaa cttataccc | 660 |
| tccaccgtga atcttgagga gtatgtgcgc gaagacgccg ctcgtgcata ctactgcccc | 720 |
| tacaagtccc gtcccaactt gcatgtcctg ctcaacactt tgccaaccg gattgtgtgg | 780 |
| gacggcgaag cccatgacgg ccacatcact gccagtggtg tcgagatcac ttccaggaac | 840 |
| ggcactgttc gtgttatcaa tgcggagaag gaagtcattg tctctgccgg tgccttgaag | 900 |
| tccccggcta tccttgaact ttctggaatt ggcaacccta gcgttcttga caagcacaac | 960 |
| atccccgtca aggtcaacct cccgactgtc ggcgagaacc ttcaggacca agtgaacagc | 1020 |
| cacatggatg catcgggcaa cacttccatc tctggaacca aggcagtctc ctaccccgat | 1080 |

-continued

```
gtctatgacg tcttcggtga cgaagccgag tcggtcgcca acagatccg tgccaacctg    1140 aagcaatacg ccgccgacac cgccaaggcc aacggaaaca ttatgaaggc cgccgatctg    1200
gagcgtctct tcgaggtcca gtatgacctt attttcaagg gcagagttcc aatcgctgaa    1260
gtcctgaact atccgggcag cgcgacgtcc gtgtttgcag aattctgggc cctccttccc    1320
ttcgctcgtg gaagtgttca catcggttct tcaaacccgg ccgagttccc tgtcatcaac    1380
cccaactatt tcatgctcga ctgggacgcg aagagctacg ttgccgttgc gaagtatatc    1440
cgccgttcgt tcgagagcta ccctctcagc agtatcgtga aggagtctac ccctggctat    1500
gatgttatcc cccggaacgc ttctgagcag agctggaaag aatgggtctt tgataagaac    1560
tatcgttcta acttccatcc cgtcggcacg gctgccatga tgcctcgtga gattggtggt    1620
gtcgtggacg agcgtctgaa tgtctatggc actacgaatg tcagagttgt agatgcttcg    1680
gtccttccat tccaggtctg cggccatttg gtgagcacac tatacgctgt ggccgaacgg    1740
gcggcggatc tcatcaaggc cgatgctggt cgtcgttag                            1779
```

```
<210> SEQ ID NO 3
<211> LENGTH: 32
<212> TYPE: DNA
<213> ORGANISM: Artificial Sequence
<220> FEATURE:
<223> OTHER INFORMATION: Synthetic construct; Primer DNA(F)

<400> SEQUENCE: 3
cgtcatggta cctccaactc cacgtccgcc aa                                   32

<210> SEQ ID NO 4
<211> LENGTH: 32
<212> TYPE: DNA
<213> ORGANISM: Artificial Sequence
<220> FEATURE:
<223> OTHER INFORMATION: Synthetic construct; Primer DNA(R)

<400> SEQUENCE: 4
agtgtactgc agctaacgac gaccagcatc gg                                   32

<210> SEQ ID NO 5
<211> LENGTH: 33
<212> TYPE: DNA
<213> ORGANISM: Artificial Sequence
<220> FEATURE:
<223> OTHER INFORMATION: Synthetic construct; Primer DNA(G73A)

<400> SEQUENCE: 5
gtcacaaacg tggatgccta cgggcttgct ttt                                  33

<210> SEQ ID NO 6
<211> LENGTH: 31
<212> TYPE: DNA
<213> ORGANISM: Artificial Sequence
<220> FEATURE:
<223> OTHER INFORMATION: Synthetic construct; Primer DNA(P527L)

<400> SEQUENCE: 6
gttctaactt ccatctcgtc ggcacggctg c                                    31

<210> SEQ ID NO 7
<211> LENGTH: 31
<212> TYPE: DNA
<213> ORGANISM: Artificial Sequence
<220> FEATURE:
<223> OTHER INFORMATION: Synthetic construct; Primer DNA(D72A)
```

<400> SEQUENCE: 7
atgtcacaaa cgtggctggc tacgggcttg c                                31

<210> SEQ ID NO 8
<211> LENGTH: 33
<212> TYPE: DNA
<213> ORGANISM: Artificial Sequence
<220> FEATURE:
<223> OTHER INFORMATION: Synthetic construct; Primer DNA(Y228H)

<400> SEQUENCE: 8
cgtgaatctt gaggagcatg tgcgcgaaga cgc                              33

<210> SEQ ID NO 9
<211> LENGTH: 35
<212> TYPE: DNA
<213> ORGANISM: Artificial Sequence
<220> FEATURE:
<223> OTHER INFORMATION: Synthetic construct; Primer DNA(G73C)

<400> SEQUENCE: 9
tcccaatgtc acaaacgtgg attgctacgg gcttg                            35

<210> SEQ ID NO 10
<211> LENGTH: 40
<212> TYPE: DNA
<213> ORGANISM: Artificial Sequence
<220> FEATURE:
<223> OTHER INFORMATION: Synthetic construct; Primer DNA(G73H)

<400> SEQUENCE: 10
caatgtcaca aacgtggatc actacgggct tgcttttggg                       40

<210> SEQ ID NO 11
<211> LENGTH: 29
<212> TYPE: DNA
<213> ORGANISM: Artificial Sequence
<220> FEATURE:
<223> OTHER INFORMATION: Synthetic construct; Primer DNA(R102H)

<400> SEQUENCE: 11
tagtcaagtg cttcatgccg gcaaggccc                                   29

<210> SEQ ID NO 12
<211> LENGTH: 40
<212> TYPE: DNA
<213> ORGANISM: Artificial Sequence
<220> FEATURE:
<223> OTHER INFORMATION: Synthetic construct; Primer DNA(D72A+G73D)

<400> SEQUENCE: 12
ccaatgtcac aaacgtggct gactacgggc ttgcttttgg                       40

<210> SEQ ID NO 13
<211> LENGTH: 35
<212> TYPE: DNA
<213> ORGANISM: Artificial Sequence
<220> FEATURE:
<223> OTHER INFORMATION: Synthetic construct; Primer DNA(G73S)

<400> SEQUENCE: 13
tcccaatgtc acaaacgtgg atagctacgg gcttg                            35

<210> SEQ ID NO 14
<211> LENGTH: 45

```
<212> TYPE: DNA
<213> ORGANISM: Artificial Sequence
<220> FEATURE:
<223> OTHER INFORMATION: Synthetic construct; Primer DNA(G73Q)

<400> SEQUENCE: 14
aacaatccca atgtcacaaa cgtggatcag tacgggcttg ctttt          45

<210> SEQ ID NO 15
<211> LENGTH: 36
<212> TYPE: DNA
<213> ORGANISM: Artificial Sequence
<220> FEATURE:
<223> OTHER INFORMATION: Synthetic construct; Primer DNA(G73W)

<400> SEQUENCE: 15
cccaatgtca caaacgtgga ttggtacggg cttgct                    36

<210> SEQ ID NO 16
<211> LENGTH: 48
<212> TYPE: DNA
<213> ORGANISM: Artificial Seqeunce
<220> FEATURE:
<223> OTHER INFORMATION: Synthetic construct; Primer DNA(G73Y)

<400> SEQUENCE: 16
ggaacaatcc caatgtcaca aacgtggatt attacgggct tgctttttg      48

<210> SEQ ID NO 17
<211> LENGTH: 38
<212> TYPE: DNA
<213> ORGANISM: Artificial Sequence
<220> FEATURE:
<223> OTHER INFORMATION: Synthetic construct; Primer DNA(G73E)

<400> SEQUENCE: 17
atgtcacaaa cgtggatgag tacgggcttg cttttggg                  38

<210> SEQ ID NO 18
<211> LENGTH: 75
<212> TYPE: DNA
<213> ORGANISM: Artificial Sequence
<220> FEATURE:
<223> OTHER INFORMATION: Synthetic construct; Primer gene1F-1

<400> SEQUENCE: 18
atgttgggaa agctctcctt cctcagtgcc ctgtccctgg cagtggcggc acctttgtcc    60
aactccacgt ccgcc                                                    75

<210> SEQ ID NO 19
<211> LENGTH: 52
<212> TYPE: DNA
<213> ORGANISM: Artificial Sequence
<220> FEATURE:
<223> OTHER INFORMATION: Synthetic construct; Primer gene1F-2

<400> SEQUENCE: 19
acgcgtcgac tgaccaattc cgcagctcgt caaaatgttg ggaaagctct cc           52

<210> SEQ ID NO 20
<211> LENGTH: 37
<212> TYPE: DNA
<213> ORGANISM: Artificial Sequence
<220> FEATURE:
<223> OTHER INFORMATION: Synthetic construct; Primer gene1R

<400> SEQUENCE: 20
```
gtgctaacga cgaccagcat cggccttgat gagatcc                           37

<210> SEQ ID NO 21
<211> LENGTH: 33
<212> TYPE: DNA
<213> ORGANISM: Artificial Sequence
<220> FEATURE:
<223> OTHER INFORMATION: Synthetic construct; Primer DNA(S37V)

<400> SEQUENCE: 21
attggaggcg gtactgtggg tttggccgtc gca                              33

<210> SEQ ID NO 22
<211> LENGTH: 33
<212> TYPE: DNA
<213> ORGANISM: Artificial Sequence
<220> FEATURE:
<223> OTHER INFORMATION: Synthetic construct; Primer DNA(S37G)

<400> SEQUENCE: 22
attggaggcg gtactggcgg tttggccgtc gca                              33

<210> SEQ ID NO 23
<211> LENGTH: 33
<212> TYPE: DNA
<213> ORGANISM: Artificial Sequence
<220> FEATURE:
<223> OTHER INFORMATION: Synthetic construct; Primer DNA(T69I)

<400> SEQUENCE: 23
aacaatccca atgtcatcaa cgtggatggc tac                              33

<210> SEQ ID NO 24
<211> LENGTH: 31
<212> TYPE: DNA
<213> ORGANISM: Artificial Sequence
<220> FEATURE:
<223> OTHER INFORMATION: Synthetic construct; Primer DNA(L76F)

<400> SEQUENCE: 24
tggatggcta cggggttcgct tttgggtctg a                               31

<210> SEQ ID NO 25
<211> LENGTH: 31
<212> TYPE: DNA
<213> ORGANISM: Artificial Seqeunce
<220> FEATURE:
<223> OTHER INFORMATION: Synthetic construct; Primer DNA(F78L)

<400> SEQUENCE: 25
gctacgggct tgctttgggg tctgacattg a                                31

<210> SEQ ID NO 26
<211> LENGTH: 33
<212> TYPE: DNA
<213> ORGANISM: Artificial Seqeunce
<220> FEATURE:
<223> OTHER INFORMATION: Synthetic construct; Primer DNA(R102V)

<400> SEQUENCE: 26
cttagtcaag tgcttgtcgc cggcaaggcc ctt                              33

<210> SEQ ID NO 27
<211> LENGTH: 33
<212> TYPE: DNA
<213> ORGANISM: Artificial Seqeunce

```
<220> FEATURE:
<223> OTHER INFORMATION: Synthetic construct; Primer DNA(N217S)

<400> SEQUENCE: 27
aagatgcgcg gcttttcctt ataccccctcc acc                               33

<210> SEQ ID NO 28
<211> LENGTH: 33
<212> TYPE: DNA
<213> ORGANISM: Artificial Seqeunce
<220> FEATURE:
<223> OTHER INFORMATION: Synthetic construct; Primer DNA(P240I)

<400> SEQUENCE: 28
cgtgcatact actggatcta caagtcccgt ccc                                33

<210> SEQ ID NO 29
<211> LENGTH: 33
<212> TYPE: DNA
<213> ORGANISM: Artificial Seqeucne
<220> FEATURE:
<223> OTHER INFORMATION: Synthetic construct; Primer DNA(P240L)

<400> SEQUENCE: 29
cgtgcatact actggttgta caagtcccgt ccc                                33

<210> SEQ ID NO 30
<211> LENGTH: 33
<212> TYPE: DNA
<213> ORGANISM: Artificial Seqeucne
<220> FEATURE:
<223> OTHER INFORMATION: Synthetic construct; Primer DNA(Q407L)

<400> SEQUENCE: 30
cgtctcttcg aggtcctgta tgaccttatt ttc                                33

<210> SEQ ID NO 31
<211> LENGTH: 33
<212> TYPE: DNA
<213> ORGANISM: Artificial Sequence
<220> FEATURE:
<223> OTHER INFORMATION: Synthetic construct; Primer DNA(Q407S)

<400> SEQUENCE: 31
cgtctcttcg aggtctgcta tgaccttatt ttc                                33

<210> SEQ ID NO 32
<211> LENGTH: 35
<212> TYPE: DNA
<213> ORGANISM: Artificial Sequence
<220> FEATURE:
<223> OTHER INFORMATION: Synthetic construct; Primer DNA(Y424S)

<400> SEQUENCE: 32
cgctgaagtc ctgaactcgc cgggcagcgc gacgt                              35

<210> SEQ ID NO 33
<211> LENGTH: 33
<212> TYPE: DNA
<213> ORGANISM: Artificial Sequence
<220> FEATURE:
<223> OTHER INFORMATION: Synthetic construct; Primer DNA(A437I)

<400> SEQUENCE: 33
tttgcagaat tctggatcct ccttcccttc gct                                33
```

```
<210> SEQ ID NO 34
<211> LENGTH: 33
<212> TYPE: DNA
<213> ORGANISM: Artificial Sequence
<220> FEATURE:
<223> OTHER INFORMATION: Synthetic construct; Primer DNA(T530A)

<400> SEQUENCE: 34
ttccatcccg tcggcgcggc tgccatgatg cct                              33
```

US 8,445,221 B2

MODIFIED GLUCOSE DEHYDROGENASE GENE

This application is a U.S. national stage of International Application No. PCT/JP2008/073689 filed Dec. 26, 2008.

TECHNICAL FIELD

The present invention relates to an FAD-conjugated glucose dehydrogenase (GLD) which requires flavin adenine dinucleotide (FAD) as a coenzyme and catalyzes a reaction of the dehydrogenation (oxidation) of a hydroxy group at the 1-position of glucose. More particularly, the invention relates to a modified GLD polypeptide having a modified substrate specificity; a polynucleotide encoding the modified GLD; a method for the production of the enzyme; and a method for the determination of glucose, a reagent composition for use in the determination of glucose, a biosensor for use in the determination of glucose, and others, each characterized by using the enzyme. Incidentally, in the description, unless otherwise specified, monosaccharides such as glucose refer to those in the D-form.

BACKGROUND ART

The blood glucose concentration is an important marker for diabetes. In the determination of a blood glucose concentration, a glucose oxidase has conventionally been used. However, such a glucose oxidase is affected by a dissolved oxygen concentration and an error is caused in the measured value. Therefore, a glucose dehydrogenase which is not affected by oxygen has also been widely used recently.

As a commercially available glucose dehydrogenase which is not affected by oxygen, a glucose dehydrogenase which requires pyrroloquinoline quinone (PQQ) as a coenzyme (PQQ-GDH) is known, however, a conventional PQQ-GDH has a disadvantage that it reacts also with sugars other than glucose such as maltose and galactose.

As a countermeasure against this disadvantage, the group of the present inventors found a novel soluble GLD which requires FAD as a coenzyme from *Aspergillus terreus* FERM BP-08578 strain (Patent document 1) and succeeded in cloning of a gene (Patent document 2). Such a GLD has unprecedented excellent properties that it is not affected by dissolved oxygen, oxidizes a hydroxy group at the 1-position of glucose, and has a low activity (enzymatic activity) for maltose and galactose.

Further, it is shown that the glucose dehydrogenases derived from *Penicillium lilacinoechinulatum* NBRC 6231, *Penicillium italicum* NBRC 32032, and *Aspergillus oryzae* TI strains disclosed in Patent document 3 and the glucose dehydrogenase derived from *Aspergillus oryzae* BB-56 strain disclosed in patent document 4 also have a low activity for maltose and galactose.

However, there was still a problem that the substrate specificity of these conventional GLDs should be improved.
Patent document 1: WO 2004/058958
Patent document 2: WO 2006/101239
Patent document 3: WO 2007/116710
Patent document 4: WO 2007/139013

DISCLOSURE OF THE INVENTION

Problems to be Solved by the Invention

Conventionally known GLDs have a disadvantage that they act on xylose, and a patient who is undergoing a xylose absorption test shows a blood glucose level higher than the actual value. Therefore, a caution not to use GLD is also given to the patient.

Accordingly, there is a need for a GLD having a higher specificity for glucose, and an object to be achieved by the invention is to provide such a GLD.

An object of the invention is to achieve the above object and to provide a novel gene (polynucleotide) encoding a modified GLD having excellent properties that it has excellent reactivity to glucose and excellent substrate recognition performance and also has a low activity for maltose and galactose and also for xylose; a method for the production of the enzyme using a transformed cell transfected with the gene; and a method for the determination of glucose, a reagent composition for use in the determination of glucose, a biosensor for use in the determination of glucose and others, each characterized by using the enzyme.

Means for Solving the Problems

The invention relates to the following aspects.
[Aspect 1]
A modified glucose dehydrogenase (GLD), comprising a substitution of at least one amino acid residue selected from the group consisting of amino acid residues at positions 37, 69, 72, 73, 76, 78, 102, 217, 228, 240, 356, 407, 424, 437, 527, and 530 in an amino acid sequence of a wild-type FAD-conjugated glucose dehydrogenase (GLD) represented by SEQ ID NO: 1, and having a decreased ratio of activity for xylose/activity for glucose as compared with the wild-type GLD.
[Aspect 2]
The modified GLD according to Aspect 1, wherein the ratio of activity for xylose/activity for glucose is decreased to 0.85 times or less of that of the wild-type GLD.
[Aspect 3]
The modified GLD according to Aspect 1 or 2, wherein the amino acid substitution is selected from the group consisting of D72A, G73D, G73A, G73S, G73C, G73Q, G73W, G73Y, G73E, G73H, R102H, Y228H, V356A, and P527L, and S37V, S37G, T69I, L76F, F78L, R102V, N217S, P240I, P240L, Q407A, Q407S, Y424S, A437I, and T530A.
[Aspect 4]
A modified glucose dehydrogenase (GLD), comprising an amino acid substitution selected from the group consisting of N64D+R102H+L250Q, G73D, Y228H+A589T, K374Q+P527L, V356A, D72A+G210S, G73A, P527L, D72A, Y228H, G73C, G73H, R102H, D72A+G73D, G73S, G73Q, G73W, G73Y, and G73E, and S37V, S37G, T69I, L76F, F78L, R102V, N217S, P240I, P240L, Q407A, Q407S, Y424S, A437I, and T530A in an amino acid sequence of a wild-type FAD-conjugated glucose dehydrogenase (GLD) represented by SEQ ID NO: 1.
[Aspect 5]
A polynucleotide encoding the modified GLD according to any one of Aspects 1 to 4.
[Aspect 6]
The polynucleotide according to Aspect 5, wherein the polynucleotide encoding the amino acid sequence of the wild-type FAD-conjugated glucose dehydrogenase (GLD) represented by SEQ ID NO: 1 has a base sequence represented by SEQ ID NO: 2.
[Aspect 7]
A recombinant vector, comprising the polynucleotide according to Aspect 5 or 6.

[Aspect 8]

A transformed cell, which is produced by using the recombinant vector according to Aspect 7.

[Aspect 9]

The transformed cell according to Aspect 8, which is *Escherichia coli* or *Aspergillus oryzae*.

[Aspect 10]

A method for the production of a modified GLD, characterized by comprising: culturing the transformed cell according to Aspect 8 or 9; and collecting a modified GLD from the resulting culture.

[Aspect 11]

A method for the determination of glucose, characterized by using the modified GLD according to any one of Aspects 1 to 4 or a modified GLD obtained by the production method according to Aspect 10.

[Aspect 12]

A reagent composition for use in the determination of glucose, characterized by comprising the modified GLD according to anyone of Aspects 1 to 4 or a modified GLD obtained by the production method according to Aspect 10.

[Aspect 13]

A biosensor for use in the determination of glucose, characterized by using the modified GLD according to any one of Aspects 1 to 4 or a modified GLD obtained by the production method according to Aspect 10.

Advantage of the Invention

By using the polynucleotide of the invention, a modified GLD having such excellent properties that it has excellent substrate recognition performance of glucose and also has a low activity for maltose and xylose can be produced uniformly in a large amount by, for example, a recombinant DNA technique.

BRIEF DESCRIPTION OF THE DRAWING

FIG. 1 shows a calibration curve for use in the determination of glucose obtained using a modified GLD of the invention.

BEST MODE FOR CARRYING OUT THE INVENTION

The modified GLD of the invention is characterized by comprising a substitution of at least one amino acid residue selected from the group consisting of amino acid residues at positions 37, 69, 72, 73, 76, 78, 102, 217, 228, 240, 356, 407, 424, 437, 527, and 530 in an amino acid sequence of a wild-type FAD-conjugated glucose dehydrogenase (GLD) represented by SEQ ID NO: 1 (containing a signal peptide) in the following Table 1 (a one-letter notation for amino acid sequences), and having a decreased ratio of activity for xylose/activity for glucose as compared with the wild-type GLD.

As a typical example of the substitution of the amino acid residue described above, an amino acid substitution selected from the group consisting of D72A, G73D, G73A, G73S, G73C, G73Q, G73W, G73Y, G73E, G73H, R102H, Y228H, V356A, and P527L, and S37V, S37G, T69I, L76F, F78L, R102V, N217S, P240I, P240L, Q407A, Q407S, Y424S, A437I, and T530A can be exemplified.

The modified GLD of the invention has a decreased activity for xylose such that the "ratio of activity for xylose/activity for glucose" (%) as defined in this description is a significant value as compared with the wild-type GLD, for example, the ratio is at least 0.85 times or less, preferably 0.5 times or less, more preferably 0.3 times or less, further more preferably 0.2 times or less of that of the wild-type GLD. Incidentally, the ratio of activity for xylose/activity for glucose varies depending on the culture conditions for a transformant, the determination conditions for an enzymatic activity, or the like, and therefore, it is necessary to determine the ratio of activity for xylose/activity for glucose (%) for the wild-type GLD and the modified GLD under the same conditions and to make a comparison.

Further, the modified GLD of the invention has an excellent characteristic that when a value of enzymatic activity for D-glucose is taken as 100%, a value of enzymatic activity for maltose (also referred to as "a ratio of activity for maltose/activity for glucose") is preferably 5% or less, more preferably 3% or less, and a value of enzymatic activity for D-galactose (also referred to as "a ratio of activity for D-galactose/activity for glucose") is preferably 5% or less, more preferably 3% or less.

Further, the modified GLD of the invention may have an amino acid sequence in which one to several amino acid residues have been further substituted, deleted, or added in the amino acid sequence represented by SEQ ID NO: 1 in addition to the above-mentioned amino acid substitution as long as it has a decreased ratio of activity for xylose/activity for glucose as compared with the wild-type GLD as described above.

As specifically described in Examples, a preferred example of the modified GLD of the invention is a modified GLD having an amino acid substitution selected from the group consisting of N64D+R102H+L250Q, G73D, Y228H+A589T, K374Q+P527L, V356A, D72A+G210S, G73A, P527L, D72A, Y228H, G73C, G73H, R102H, D72A+G73D, G73S, G73Q, G73W, G73Y, and G73E, and S37V, S37G, T69I, L76F, F78L, R102V, N217S, P240I, P240L, Q407A, Q407S, Y424S, A437I, and T530A, and an arbitrary combination thereof in the amino acid sequence of the wild-type GLD represented by SEQ ID NO: 1.

As one example of the polynucleotide encoding the modified GLD of the invention, a polynucleotide having a base sequence represented by SEQ ID NO: 2 (Table 2) which is a polynucleotide encoding the amino acid sequence of the wild-type GLD represented by SEQ ID NO: 1 (Table 1) can be exemplified. Other than this, a different codon may be used as long as the codon encodes the same amino acid residue. For example, a usage codon can be appropriately optimized depending on the kind of a host cell to be transformed with the polynucleotide or the like.

TABLE 1

MLGKLSFLSALSLAVAAPLSNSTSAKYDYIVIGGGTSGLAVANRLSEDPN

VNVLILEAGGSVWNNPNVTNVDGYGLAFGSDIDWQYQSVNQPYGGNLSQV

LRAGKALGGTSTINGMAYTRAEDVQIDAWETIGNTGWTWKNLFPYYRKSE

NFTVPTKSQTSLGASYEAGAHGHEGPLDVAFTQIESNNLTTYLNRTFQGM

GLPWTEDVNGGKMRGFNLYPSTVNLEEYVREDAARAYYWPYKSRPNLHVL

LNTFANRIVWDGEAHDGHITASGVEITSRNGTVRVINAEKEVIVSAGALK

SPAILELSGIGNPSVLDKHNIPVKVNLPTVGENLQDQVNSHMDASGNTSI

SGTKAVSYPDVYDVFGDEAESVAKQIRANLKQYAADTAKANGNIMKAADL

ERLFEVQYDLIFKGRVPIAEVLNYPGSATSVFAEFWALLPFARGSVHIGS

SNPAEFPVINPNYFMLDWDAKSYVAVAKYIRRSFESYPLSSIVKESTPGY

TABLE 1-continued

DVIPRNASEQSWKEWVFDKNYRSNFHPVGTAAMMPREIGGVVDERLNVYG

TTNVRVVDASVLPFQVCGHLVSTLYAVAERAADLIKADAGRR (592AA)

TABLE 2

```
atgttgggaaagctctccttcctcagtgccctgtcctggcagtggcggc
acctttgtccaactccacgtccgccaaatatgattatatcgttattggag
gcggtactagcggtttggccgtcgcaaaccgtctatcggaggatccaaac
gtgaacgtactcattctggaggccggtggctcggtctggaacaatcccaa
tgtcacaaacgtggatggctacgggcttgcttttgggtctgacattgact
ggcaataccagtccgtcaaccagccatatggaggcaaccttagtcaagtg
cttcgtgccggcaaggcccttggtggtactagtactatcaatggcatggc
ctatacgcgcgccgaggatgtccagatcgacgcctgggaaaccattggca
acacaggatggacgtggaagaatctgttcccttactatcggaagagcgag
aactttactgtccctaccaaatcgcagacctctcttggagcgtcgtatga
agctggagcccacggccacgagggtccccttgacgttgccttcactcaga
tcgagtcgaacaacctgaccacttacctcaaccgtaccttccagggcatg
ggactcccatggacggaggacgtcaatggcggaaagatgcgcggctttaa
cttataccctccaccgtgaatcttgaggagtatgtgcgcgaagacgccg
ctcgtgcatactactggccctacaagtcccgtcccaacttgcatgtcctg
ctcaacacttttgccaaccggattgtgtgggacggcgaagcccatgacgg
ccacatcactgccagtggtgtcgagatcacttccaggaacggcactgttc
gtgttatcaatgcggagaaggaagtcattgtctctgccggtgccttgaag
tccccggctatccttgaactttctggaattggcaaccctagcgttcttga
caagcacaacatccccgtcaaggtcaacctcccgactgtcggcgagaacc
ttcaggaccaagtgaacagccacatggatgcatcgggcaacacttccatc
tctggaaccaaggcagtctcctaccccgatgtctatgacgtcttcggtga
cgaagccgagtcggtcgccaaacagatccgtgccaacctgaagcaatacg
ccgccgacaccgccaaggccaacggaaacattatgaaggccgccgatctg
gagcgtctcttcgaggtccagtatgaccttattttcaagggcagagttcc
aatcgctgaagtcctgaactatccgggcagcgcgacgtccgtgtttgcag
aattctgggccctccttcccttcgctcgtggaagtgttcacatcggttct
tcaaaccggccgagttccctgtcatcaacccaactatttcatgctcga
ctgggacgcgaagagctacgttgccgttgcgaagtatatccgccgttcgt
tcgagagctaccctctcagcagtatcgtgaaggagtctaccctggctat
gatgttatccccggaacgcttctgagcagagctggaaagaatgggtctt
tgataagaactatcgttctaacttccatcccgtcggcacggctgccatga
tgcctcgtgagattggtggtgtcgtggacgagcgtctgaatgtctatggc
actacgaatgtcagagttgtagatgcttcggtccttccattccaggtctg
cggccatttggtgagcacactatacgctgtggccgaacgggcggcggatc
tcatcaaggccgatgctggtcgtcgttag (1779 bp)
```

Incidentally, in the invention, the "polynucleotide" refers to a molecule in which 100 or more phosphate esters of nucleosides in which a purine or a pyrimidine is attached to a sugar via a β-N-glycosidic bond (ATP (adenosine triphosphate), GTP (guanosine triphosphate), CTP (cytidine triphosphate), or UTP (uridine triphosphate); or dATP (deoxyadenosine triphosphate), dGTP (deoxyguanosine triphosphate), dCTP (deoxycytidine triphosphate), or dTTP (deoxythymidine triphosphate). Specific examples thereof include a chromosomal DNA (a DNA containing an intron) encoding the modified GLD of the invention, a mRNA transcribed from the chromosomal DNA, a cDNA synthesized from the mRNA, and a polynucleotide amplified by PCR using any of these as a template. An "oligonucleotide" refers to a molecule in which 2 to 99 nucleotides are linked to one another. Further, the "polypeptide" refers to a molecule formed from 30 or more amino acid residues which are linked to one another via an amide bond (peptide bond) or an unnatural residual linkage, and also those with the addition of a sugar chain, those subjected to artificial chemical modification, and the like are included. Further, in the polynucleotide of the invention, also a base sequence encoding a signal sequence of the modified GLD can be appropriately included depending on the kind of a transformed cell or the like.

The polynucleotide of the invention can be easily prepared by an arbitrary method known to those skilled in the art. For example, as specifically described in Examples of this description, a wild-type GLD gene is isolated from a plasmid containing a polynucleotide having a base sequence represented by SEQ ID NO: 2, and introducing a random mutation or a site-specific mutation by utilizing any of various PCR methods known to those skilled in the art using an appropriate oligonucleotide primer (probe) set based on the isolated gene, whereby the polynucleotide encoding the modified GLD of the invention can be prepared.

Further, the polynucleotide of the invention can be synthesized in vitro by a well-known chemical synthesis technique as described in a document (such as Carruthers (1982) Cold Spring Harbor Symp. Quant. Biol. 47: 411-418; Adams (1983) J. Am. Chem. Soc. 105: 661; Belousov (1997) Nucleic Acid Res. 25: 3440-3444; Frenkel (1995) Free Radic. Biol. Med. 19: 373-380; Blommers (1994) Biochemistry 33: 7886-7896; Narang (1979) Meth. Enzymol. 68: 90; Brown (1979) Meth. Enzymol. 68: 109; Beaucage (1981) Tetra. Lett. 22: 1859; or U.S. Pat. No. 4,458,066).

The recombinant vector of the invention can be prepared by an arbitrary method known to those skilled in the art using an appropriate cloning vector or expression vector depending on the kind of a polynucleotide to be used as an insert, an intended use thereof, or the like. For example, in the case where the modified GLD of the invention is produced using a cDNA or an ORF region thereof as an insert, an expression vector for in vitro transcription, or also an expression vector suitable for the respective prokaryotic cells such as *Escherichia coli* and *Bacillus subtilis*; and eukaryotic cells such as yeasts, filamentous fungi (such as molds), insect cells, and mammalian cells can be used.

As the transformed cell of the invention, for example, a prokaryotic cell such as *Escherichia coli* or *Bacillus subtilis*; a eukaryotic cell such as a yeast, a mold, an insect cell, or a mammalian cell; or the like can be used. As for such a cell, a host can be suitably selected in accordance with the need of a sugar chain or other peptide modification for the modified GLD. Such a transformed cell can be prepared by introducing a recombinant vector into a cell by an arbitrary method known to those skilled in the art such as an electroporation method, a calcium phosphate method, a liposome method, or a DEAE dextran method. Specific examples of the recombinant vector and the transformed cell include a recombinant vector shown in the below-mentioned Examples and a transformed *Escherichia coli* and a transformed mold prepared with this vector.

In the case where the modified GLD of the invention is produced by expressing a DNA in a microorganism such as *Escherichia coli*, a recombinant expression vector in which the above-mentioned polynucleotide has been introduced into an expression vector having an origin, a promoter, a ribosome-binding site, a DNA cloning site, a terminator sequence, and the like and replicable in the microorganism is prepared, a host cell is transformed with this expression vector, and the resulting transformant is cultured, whereby the modified GLD can be produced in a large amount in the microorganism. At this time, if a start codon and a stop codon are introduced upstream and downstream of an arbitrary coding region and the DNA is expressed, a modified GLD fragment containing the arbitrary region can also be obtained. Alternatively, the enzyme can also be expressed as a fusion protein with another protein. By cleaving this fusion protein with an appropriate protease, the target modified GLD can also be obtained. Examples of the expression vector for *Escherichia coli* include a pUC system, pBluescript II, a pET expression system, a pGEX expression system, and a pCold expression system.

Alternatively, in the case where the modified GLD of the invention is produced by expressing it in a eukaryotic cell, a recombinant vector is prepared by inserting the above-mentioned polynucleotide into an expression vector for a eukaryotic cell having a promoter, a splicing region, a poly(A) addition site, and the like, and the resulting recombinant vector is introduced into a eukaryotic cell, whereby the modified GLD can be produced in the eukaryotic cell. The polynucleotide can be maintained in a cell in a state of a plasmid or the like, or can be maintained by incorporating the polynucleotide into a chromosome. Examples of the expression vector include pKA1, pCDM8, pSVK3, pSVL, pBK-CMV, pBK-RSV, an EBV vector, pRS, and pYE82. Further, if pIND/V5-His, pFLAG-CMV-2, pEGFP-N1, pEGFP-C1, or the like is used as the expression vector, an FAD-conjugated glucose dehydrogenase polypeptide can also be expressed as a fusion protein to which any of a variety of tags such as a His tag, a FLAG tag, or GFP has been attached. As the eukaryotic cell, a cultured mammalian cell such as a monkey kidney cell COS-7, or a Chinese hamster ovary cell CHO; a budding yeast, a fission yeast, a mold, a silkworm cell, or a *Xenopus* oocyte is generally used, however, any kind of eukaryotic cell may be used as long as it can express the modified GLD of the invention. In order to introduce the expression vector into the eukaryotic cell, a known method such as an electroporation method, a calcium phosphate method, a liposome method, or a DEAE dextran method can be used.

In particular, cloning in which an appropriate *Aspergillus oryzae* strain is transformed with a recombinant vector derived from *Aspergillus oryzae* containing a polynucleotide encoding the modified GLD of the invention is preferred.

In order to collect, in other words, isolate and purify the target protein from a culture (such as microbial cells or a culture broth or a culture medium composition containing the enzyme secreted to the outside of microbial cells) after the modified GLD of the invention is expressed in a prokaryotic cell or a eukaryotic cell, known separation procedures can be combined. Examples of such procedures include a treatment with a denaturant such as urea or a surfactant, a heat treatment, a pH treatment, an ultrasonication treatment, enzymatic digestion, salting out, a solvent sedimentation method, dialysis, centrifugal separation, ultrafiltration, gel filtration, SDS-PAGE, isoelectric focusing, ion exchange chromatography, hydrophobic chromatography, reverse-phase chromatography, and affinity chromatography (also including a method utilizing a tag sequence, and a method using a polyclonal antibody or a monoclonal antibody specific for the modified GLD). By using such a method, the modified GLD of the invention can be produced in a large amount.

Further, the modified GLD of the invention can be produced in vitro by preparing an RNA through in vitro transcription from a vector containing the polynucleotide (a cDNA or a coding region thereof) of the invention and performing in vitro translation using the RNA as a template.

In the case where the modified GLD is produced by in vitro expression, the above-mentioned polynucleotide is inserted into a vector having a promoter to which an RNA polymerase can bind thereby preparing a recombinant vector, and this vector is added to an in vitro translation system such as a rabbit reticulocyte lysate or a wheat germ extract including an RNA polymerase corresponding to the promoter, whereby the modified GLD can be produced in vitro. Examples of the promoter to which an RNA polymerase can bind include T3, T7, and SP6. Examples of the vector containing such a promoter include pKA1, pCDM8, pT3/T718, pT7/319, and pBluescript II.

The modified GLD of the invention which can be produced by the method described above is an enzyme which catalyzes a reaction of the dehydrogenation of glucose in the presence of an electron acceptor, and therefore, the use thereof is not particularly limited as long as a change caused by this reaction can be utilized. For example, it can be used in the medical field or the clinical field such as the use in the determination of glucose in a sample containing a biological material, a reagent for use in the determination thereof, or a reagent for use in the elimination thereof, and also it can be used in the production of a substance using a coenzyme-conjugated glucose dehydrogenase.

The reagent composition for use in the determination of glucose of the invention may be formulated into a single reagent by mixing all the components, or in the case where the reagent composition contains components interfering with each other, the respective components may be separated so as to provide suitable combinations. Further, the reagent composition may be prepared as a reagent in the form of a solution or a powder, and moreover, it may be prepared as a test paper or a film for use in the analysis by being incorporated in an appropriate support such as a filter paper or a film. Incidentally, a standard reagent containing a deproteinizing agent such as perchloric acid or a fixed amount of glucose may be attached. The amount of the enzyme in this composition is preferably about 0.1 to 50 units per sample. Examples of a specimen to be determined for glucose include plasma, serum, spinal fluid, saliva, and urine.

The biosensor of the invention is a glucose sensor which determines a glucose concentration in a sample liquid using a reaction layer containing the modified GLD of the invention as an enzyme. The biosensor is produced by, for example, forming an electrode system comprising a working electrode, its counter electrode, and a reference electrode on an insulating base plate using a method such as screen printing, and forming an enzyme reaction layer containing a hydrophilic polymer, an oxidoreductase, and an electron acceptor on this electrode system in contact therewith. When a sample liquid containing a substrate is dropped on the enzyme reaction layer of this biosensor, the enzyme reaction layer is dissolved and the enzyme and the substrate are reacted with each other, and accompanying the reaction, the electron acceptor is reduced. After completion of the enzymatic reaction, the reduced electron acceptor is electrochemically oxidized. At this time, this biosensor can determine the substrate concentration in the sample liquid from the oxidation current value obtained. In addition, other than this, a biosensor of a type that detects a coloring intensity, a pH change, or the like can also be constructed.

As the electron acceptor of the biosensor, a chemical substance having an excellent ability to donate and accept electrons can be used. The chemical substance having an excellent ability to donate and accept electrons is a chemical substance generally called "an electron carrier", "a mediator", or "a redox mediator", and as a chemical substance corresponding to such a substance, an electron carrier or a redox mediator cited in, for example, JP-T-2002-526759 or the like may be used. Specific examples thereof include an osmium compound, a quinone compound, and a ferricyan compound.

In the determination of the activity of GLD, the enzyme is preferably used by appropriately diluting it such that the final concentration thereof is 0.1 to 1.0 unit/mL. Incidentally, the unit of the enzymatic activity (unit) of the enzyme is an enzymatic activity that oxidizes 1 μmol of glucose per minute. The enzymatic activity of GLD can be determined by the following method.

[Method for Determination of Enzymatic Activity]

1.0 mL of 0.1 M potassium phosphate buffer (pH 7.0), 1.0 mL of 1.0 M D-glucose, 0.14 mL of 3 mM 2,6-dichlorophenol indophenol (hereinafter referred to as DCIP), 0.2 mL of 3 mM 1-methoxy-5-methylphenazinium methylsulfate, and 0.61 mL of water are added to a 3-mL quartz cell (light path length: 1 cm), and the cell is placed in a spectrophotometer provided with a thermostat cell holder and incubated at 37° C. for 10 minutes. Thereafter, 0.05 mL of an enzyme solution is added to the cell, and then, a change in the absorbance of DCIP at 600 nm (ΔABS/min) is determined. The molar extinction coefficient of DCIP at pH 7.0 is taken as $16.3 \times 10^3$ $cm^{-1}M^{-1}$, and the enzymatic activity to reduce 1 μmol of DCIP per minute is substantially equivalent to 1 unit of the enzymatic activity. Therefore, the enzymatic activity was determined from the change in the absorbance according to the following equation.

$$\text{Enzymatic activity(unit/mL)} = (-\Delta ABS/16.3) \times 3.0/0.05 \times (\text{Dilution ratio of enzyme}) \quad \text{[Equation 1]}$$

In the same manner as the above-mentioned procedure, the enzymatic activity to oxidize 1 μmol of xylose, maltose, or galactose per minute can be determined using the same concentration of D-xylose (manufactured by Sigma, Inc.), maltose monohydrate (manufactured by Nacalai Tesque), or D-galactose (manufactured by Wako Pure Chemical Industries, Ltd.) in place of D-glucose.

Further, in the case where the enzymatic activity (U) to oxidize glucose is taken as 100%, the enzymatic activity (relative activity) to oxidize xylose is defined as the "ratio of activity for xylose/activity for glucose" (%).

Similarly, in the case where the enzymatic activity (U) to oxidize glucose is taken as 100%, the enzymatic activity (relative activity) to oxidize maltose or galactose is defined as the "ratio of activity for maltose/activity for glucose" (%) or the "ratio of activity for galactose/activity for glucose" (%).

Incidentally, the determination of the activity can also be performed using a plate reader. In this case, a change in the absorbance at 600 nm is determined using a reaction reagent having the same composition as described above and an appropriately diluted enzyme, and converted in proportion to a change in the absorbance of an enzyme solution for which the enzymatic activity has already been known by the above-mentioned activity determination procedure using a quartz cell, whereby the enzymatic activity of the enzyme solution can be calculated.

In the determination of the protein concentration of this enzyme, the enzyme is preferably used by appropriately diluting it such that the final concentration thereof is 0.2 to 0.9 mg/mL. The protein concentration in the invention can be determined by the calculation from a calibration curve prepared by using bovine serum albumin (BSA, manufactured by Wako Pure Chemical Industries, Ltd., for biochemical purpose) as a standard substance using a Bio-Rad Protein Assay, which is a protein concentration determination kit and can be purchased from Bio-Rad Laboratories, Inc. Japan according to the instruction attached thereto.

Incidentally, various techniques used for implementing the invention can be easily and surely carried out by those skilled in the art based on publicly known documents and the like exclusive of techniques the sources of which are indicated specifically. For example, the genetic engineering and molecular biological techniques can be carried out based on the methods described in Sambrook and Maniatis, in Molecular Cloning: A Laboratory Manual, Cold Spring Harbor Laboratory Press, New York, 1989; Ausubel, F. M. et al., Current Protocols in Molecular Biology, John Wiley & Sons, New York, N.Y., 1995; and the like or the methods described in the references cited therein or methods substantially equivalent thereto or modified methods thereof. In addition, the terms in the invention are basically in accordance with IUPAC-IUB Commission on Biochemical Nomenclature or the meanings of terms conventionally used in the art.

Hereinafter, the invention will be more specifically described with reference to Examples. However, the technical scope of the invention is by no means limited to the description thereof. Further, the contents described in the documents cited in this description constitute the disclosure of this description as a part thereof.

EXAMPLE 1

Acquisition of Wild-Type GLD Gene

A plasmid pCGLD containing the wild-type GLD gene (SEQ ID NO: 2) whose entire base sequence is disclosed in Patent document 2 was isolated from *Eschelichia coli* JM109/pCGLD (FERM BP-10243). This can also be obtained by isolating a GLD gene derived from *Aspergillus terreus* FERM BP-08578 strain disclosed in patent document 1 by a common procedure and inserting the GLD gene into the KpnI-PstI sites in the multicloning site of a plasmid vector pCold III commercially available from Takara Bio Inc. in the form in which a region encoding a signal sequence (an amino acid sequence of amino acid residues 1 to 19 of SEQ ID NO: 1) has been removed.

EXAMPLE 2

Acquisition of Transformant Having Modified GLD Gene Having Random Mutation Introduced Therein In order to introduce a random mutation into a GLD gene, oligonucleotides as shown below were designed and synthesized. Incidentally, a primer DNA (F) has a restriction enzyme KpnI site, and a primer DNA (R) has a restriction enzyme RstI site.
Primer DNA (F): 5' cgtcatggtacctccaactccacgtccgccaa 3' (SEQ ID NO: 3)
Primer DNA (R): 5' agtgtactgcagctaacgacgaccagcatcgg 3'(SEQ ID NO: 4)

Using the plasmid pCGLD containing the wild-type GLD gene (SEQ ID NO: 2) obtained in Example 1, the primer DNA (F) represented by SEQ ID NO: 3 and the primer DNA (R) represented by SEQ ID NO: 4 synthesized in Example 2 and also using a GeneMorph II Random Mutagenesis Kit (manufactured by Stratagene, Inc.), a plasmid into which a random mutation was introduced was obtained according to an experimental procedure attached to the kit. After E. coli JM109 Competent Cells (manufactured by Takara Bio Inc.) used as a host were subjected to transformation, the resulting cells were plated on an LB agar plate containing ampicillin sodium (manufactured by Wako Pure Chemical Industries, Ltd.) serving as a selection marker at a concentration of 50 µg/mL and cultured overnight at 37° C., whereby transformants were obtained.

EXAMPLE 3

Evaluation of Enzymatic Activity of GLD in Transformant Having Modified GLD Gene Having Random Mutation Introduced Therein A solution A containing 1.2% (w/v) tryptone (manufactured by BD), 2.4% (w/v) yeast extract (manufactured by BD), 5% (w/v) glycerin (manufactured by Nacalai Tesque), and water was prepared by an autoclave treatment at 121° C. for minutes, and a solution B containing 2.3% potassium dihydrogen phosphate (manufactured by Nacalai Tesque), 12.5% dipotassium hydrogen phosphate (manufactured by Nacalai Tesque), and water was prepared by filtration using a 0.45 µm filter (manufactured by Advantec, Inc.). The solution A and the solution B were mixed in a sterile environment such that A:B=9:1, whereby a TB medium was prepared.

Into each well of a 96-well microplate (manufactured by Nunc, Inc.), 150 µL of the TB medium was dispensed, and the transformant colonies obtained in Example 2 were inoculated thereinto one by one.

After shaking culture at 37° C. and 1,000 rpm for 5 hours, the culture temperature was shifted to 15° C., and shaking was performed at 1,000 rpm for 30 minutes. Thereafter, 25 µL of an aqueous solution of isopropyl-β-D-1-thiogalactopyranoside (manufactured by Sigma-Aldrich Japan KK) was added thereto to give a final concentration of 0.1 mM, and shaking culture was performed again at 15° C. and 1,000 rpm for 13 hours.

The transformed cells after culture were collected by centrifugation, washed with distilled water, and centrifuged again. To the resulting microbial cells, 50 µL per well of CelLytic B Cell Lysis Reagent (manufactured by Sigma, Inc.) was added, and the mixture was left as such at 25° C. for 30 minutes. Then, the mixture was centrifuged and the supernatant was collected and used as a cell-free extract.

According to the above-mentioned method for the determination of enzymatic activity, the enzymatic activity of GLD in the cell-free extract was confirmed. Mutant strains in which the enzymatic activity (U/mL-b) of GLD per mL of the culture broth in the case where D-glucose was used as a substrate did not decreased to one-tenth or less of that of the wild-type strain and the ratio of activity for xylose/activity for glucose (Xyl/Glc) dominantly decreased as compared with that of the wild-type strain were selected and subjected to a genetic analysis. The results were as shown in Table 3.

TABLE 3

| No. | Position of Gene Mutation | Position of Amino Acid Mutation | GLD Activity (U/mL-b) | Xyl/Glc (%) | Ratio of Xyl/Glc (wild-type GLD = 1) |
|---|---|---|---|---|---|
| wt | Non-Mutation | Non-Mutation | 0.75 | 13.6 | 1 |
| R14 | A190G + G305A + T749A + T849A | N64D + R102H + L250Q | 1.20 | 4.46 | 0.33 |
| R25 | G218A | G73D | 0.43 | 5.09 | 0.37 |
| R29 | T498C + T682C + G1765A | Y228H + A589T | 0.52 | 10.6 | 0.78 |
| R30 | A1120C + C1580T | K374Q + P527L | 0.42 | 8.49 | 0.62 |
| R31 | T537A + T1067C | V356A | 0.71 | 7.22 | 0.53 |
| R44 | A215C + G628A + C1407T | D72A + G210S | 0.67 | 10.8 | 0.79 |

EXAMPLE 4

Acquisition of Transformant Having Modified GLD Gene Having Site-Specific Substitution Mutation Introduced Therein: Part 1

In order to introduce a site-specific substitution mutation into a GLD gene, oligonucleotides as shown below were designed and synthesized.

```
Primer DNA (G73A):
5' gtcacaaacgtggatgcctacgggcttgctttt 3'           (SEQ ID NO: 5)

Primer DNA (P527L):
5' gttctaacttccatctcgtcggcacggctgc 3'             (SEQ ID NO: 6)

Primer DNA (D72A):
5' atgtcacaaacgtggctggctacgggcttgc 3'             (SEQ ID NO: 7)
```

-continued

Primer DNA (Y228H):
5' cgtgaatcttgaggagcatgtgcgcgaagacgc 3'          (SEQ ID NO: 8)

Primer DNA (G73C):
5' tcccaatgtcacaaacgtggattgctacgggcttg 3'        (SEQ ID NO: 9)

Primer DNA (G73H):
5' caatgtcacaaacgtggatcactacgggcttgcttttggg 3'   (SEQ ID NO: 10)

Primer DNA (R102H):
5' tagtcaagtgcttcatgccggcaaggccc 3'              (SEQ ID NO: 11)

Primer DNA (D72A + G73D):
5' ccaatgtcacaaacgtggctgactacgggcttgcttttgg 3'   (SEQ ID NO: 12)

Primer DNA (G73S):
5' tcccaatgtcacaaacgtggatagctacgggcttg 3'        (SEQ ID NO: 13)

Primer DNA (G73Q):
5' aacaatcccaatgtcacaaacgtggatcagtacgggcttgcttttt 3'  (SEQ ID NO: 14)

Primer DNA (G73W):
5'cccaatgtcacaaacgtggattggtacgggcttgct 3'        (SEQ ID NO: 15)

Primer DNA (G73Y):
5' ggaacaatcccaatgtcacaaacgtg-
gattattacgggcttgcttttg 3'                        (SEQ ID NO: 16)

Primer DNA (G73E):
5' atgtcacaaacgtggatgagtacgggcttgcttttggg 3'     (SEQ ID NO: 17)

EXAMPLE 5

Using the plasmid pCGLD containing the wild-type GLD gene obtained in Example 1, the primer DNA (G73A) represented by SEQ ID NO: 5 synthesized in Example 4, and a synthetic oligonucleotide complementary to the primer DNA and also using a QuikChange II Site-Directed Mutagenesis Kit (manufactured by Stratagene, Inc.), a plasmid into which a substitution mutation was introduced was obtained according to an experimental procedure attached to the kit. After *E. coli* JM109 Competent Cells (manufactured by Takara Bio Inc.) used as a host was subjected to transformation, the resulting cells were plated on an LB agar (manufactured by BD) plate containing ampicillin sodium (manufactured by Wako Pure Chemical Industries, Ltd.) serving as a selection marker at 50 μg/mL and cultured overnight at 37° C., whereby a transformant having a modified GLD gene encoding a modified GLD with a substitution of glycine with alanine at position 73 of the amino acid sequence of the wild-type GLD was obtained.

In the same manner as the above-mentioned method, a plasmid into which each substitution mutation was introduced was obtained using the plasmid pCGLD containing the wild-type GLD gene, each of the primer DNAs represented by SEQ ID NOS: to 17 synthesized in Example 4, and a synthetic oligonucleotide complementary to each of the primer DNAs. Transformation was also performed in the same manner as described above, and a transformant having a modified GLD gene encoding each modified GLD with a substitution of a part of the amino acid sequence of the wild-type GLD was obtained.

EXAMPLE 6

Evaluation of Enzymatic Activity of GLD in Transformant Having Modified GLD Gene Having Site-Specific Substitution Mutation Introduced Therein: Part 1

In the same manner as the procedure described in Example 3, the transformants obtained in Example 5 were cultured, and the enzymatic activity of GLD in each of the cell-free extracts was determined and evaluated. Mutant strains in which the enzymatic activity (U/mL-b) of GLD per mL of the culture broth in the case where D-glucose was used as a substrate was maintained to a level of one-tenth or more of that of the wild-type strain GLD and the ratio of activity for xylose/activity for glucose (Xyl/Glc) dominantly decreased as compared with that of the wild-type strain were selected and subjected to a genetic analysis. The results are shown in Table 4.

TABLE 4

| No. | Oligonucleotide Primer No. | Position of Amino Acid Mutation | GLD Activity (U/mL-b) | Xyl/Glc (%) | Ratio of Xyl/Glc (wild-type GLD = 1) |
|---|---|---|---|---|---|
| wt | — | Non Mutation | 0.75 | 13.6 | 1 |
| S3 | 5 | G73A | 0.97 | 4.85 | 0.36 |
| S4 | 6 | P527L | 0.26 | 9.84 | 0.72 |
| S5 | 7 | D72A | 0.45 | 10.1 | 0.74 |
| S12 | 8 | Y228H | 0.82 | 11.5 | 0.85 |
| S17 | 9 | G73C | 0.38 | 3.16 | 0.23 |
| S23 | 10 | G73H | 0.58 | 3.08 | 0.23 |
| S32 | 11 | R102H | 0.59 | 5.36 | 0.39 |

EXAMPLE 7

Evaluation of Enzymatic Activity of GLD in Transformant Having Modified GLD Gene Having Site-Specific Substitution Mutation Introduced Therein: Part 2

The transformants obtained in Example 5 were cultured in the same manner as the procedure described in Example 3 using a medium prepared by subjecting a medium (adjusted to a pH of 7.0 with NaOH) containing 4% (w/v) tryptone (manufactured by BD), 2% (w/v) yeast extract (manufactured by BD), 4% (w/v) glycerin (manufactured by Nacalai Tesque), and water to an autoclave treatment at 121° C. for 15 minutes in place of the TB medium, and the enzymatic activity of GLD in each of the cell-free extracts was determined and evaluated. Mutant strains in which the enzymatic activity (U/mL-b) of GLD per mL of the culture broth in the case where D-glucose was used as a substrate was maintained to a level of one-tenth or more of that of the wild-type strain GLD and the ratio of activity for xylose/activity for glucose (Xyl/Glc) dominantly decreased as compared with that of the wild-type strain were selected and subjected to a genetic analysis. The results are shown in Table 5.

TABLE 5

| No. | Oligonucleotide Primer No. | Position of Amino Acid Mutation | GLD Activity (U/mL-b) | Xyl/Glc (%) | Ratio of Xyl/Glc (wild-type GLD = 1) |
|---|---|---|---|---|---|
| wt | — | Non Mutation | 3.28 | 13.3 | 1 |
| S8 | 12 | D72A + G73D | 1.18 | 5.41 | 0.41 |
| S16 | 13 | G73S | 1.88 | 6.78 | 0.51 |
| S18 | 14 | G73Q | 1.38 | 5.82 | 0.44 |
| S20 | 15 | G73W | 0.69 | 8.88 | 0.67 |
| S21 | 16 | G73Y | 1.13 | 6.13 | 0.46 |
| S22 | 17 | G73E | 0.76 | 8.37 | 0.63 |

EXAMPLE 8

Cloning of Modified GLD Gene in Transformant into *Aspergillus oryzae*

Among the transformants obtained in Example 2, using the transformant (R30 strain) having a modified GLD gene encoding a modified GLD with a substitution of lysine with glutamine at position 374 and a substitution of proline with leucine at position 527 of the amino acid sequence of the wild-type GLD, a plasmid containing the modified GLD gene was isolated by a common procedure.

Similarly, among the transformants obtained in Example 2, using the transformant (R25 strain) having a modified GLD gene encoding a modified GLD with a substitution of glycine with aspartic acid at position 73 of the amino acid sequence of the wild-type GLD, a plasmid containing the modified GLD gene was isolated by a common procedure.

In the same manner, among the transformants obtained in Example 5, using the transformant (S32 strain) having a modified GLD gene encoding a modified GLD with a substitution of arginine with histidine at position 102 of the amino acid sequence of the wild-type GLD, a plasmid containing the modified GLD gene was isolated by a common procedure.

Further, in the same manner, among the transformants obtained in Example 5, using the transformant (S16 strain) having a modified GLD gene encoding a modified GLD with a substitution of glycine with serine at position 73 of the amino acid sequence of the wild-type GLD, a plasmid containing the modified GLD gene was isolated by a common procedure.

EXAMPLE 9

The modified GLD genes were amplified by PCR using the plasmids containing the respective modified GLD genes obtained in Example 8 as templates and also using the following primers (first, the primers 1 and 3 were used, and thereafter the primers 2 and 3 were used) synthesized based on the base sequence of a GLD gene derived from *Aspergillus terreus* FERM BP-08578 strain disclosed in Patent document 1.

1. gene 1F-1:
(SEQ ID NO: 18)
5'-atgttgggaaagctctccttcctcagtgccctgtccctggcagtggc ggcacctttgtccaactccacgtccgcc-3'

2. gene 1F-2:
(SEQ ID NO: 19)
5'-(acgcgtcgac)<u>tgaccaattccgcagctcgtcaaa</u>atgttgggaaa gctctcc-3'

3. gene 1R:
(SEQ ID NO: 20)
5'-(gtg)ctaacgacgaccagcatcggccttgatgagatcc-3'

(F: 5' side, R: 3' side, bases in the parenthesis: restriction enzyme cleavage sites, underlined bases: enoA 5'-UTR, others: ORF)

As a host to be used, *Aspergillus oryzae* NS4 strain (derived from RIB 40 strain) was used. This strain was bred in Brewery Laboratory in 1997 as described in a publicly known document 1 (Biosci. Biotech. Biochem., 61 (8), 1367-1369, 1997) and has been used in the analysis of transcription factors, the breeding of high-producing strains of various enzymes, and the like, and those for distribution are available.

For this strain, a modified amylase gene promoter derived from *Aspergillus oryzae* described in a publicly known document 2 (Development of the heterologous gene expression system for *Aspergillus* species, MINETOKI Toshitaka, Chemistry & Biology, 38, 12, pp. 831-838, 2000) was used, and the above-mentioned modified GLD gene was ligated to downstream of the promoter, whereby a vector which can express this gene was prepared.

Transformation was performed basically in accordance with the methods described in the publicly known document 2 and a publicly known document 3 (Genetic engineering technology of Koji mold for sake, GOMI Katsuya, Journal of the Brewing Society of Japan, pp. 494-502, 2000), whereby a transformant was obtained.

Comparative Example

Cloning of Wild-Type GLD Gene (SEQ ID NO: 1) into *Aspergillus oryzae*

A vector having the wild-type GLD gene (SEQ ID NO: 1) was prepared in the same manner as the method described in Example 8 using the plasmid pCGLD obtained in Example 1, and *Aspergillus oryzae* NS4 strain was transformed with the vector, whereby a transformant was obtained.

EXAMPLE 10

Preparation of Enzyme Solution from Transformed *Aspergillus oryzae*

Each of the transformants obtained in Example 9 and Comparative example was subjected to shaking culture at 30° C. for 3 days using 20 mL of a liquid culture medium at pH 6.0 containing 1% (w/v) glucose (manufactured by Wako Pure Chemical Industries, Ltd.), 2% (w/v) defatted soybean (manufactured by Nihon Syokuhan-Sya), 0.5% (w/v) corn steep liquor (manufactured by San-ei Sucrochemical Co., Ltd.), 0.1% (w/v) magnesium sulfate (manufactured by Nacalai Tesque), and water. After completion of the culture, the culture broth was centrifuged and the culture supernatant was collected.

The collected culture supernatant was filtered using a 10 μm membrane filter (manufactured by Advantec, Inc.), whereby an enzyme solution showing a band of about 81 kDa in SDS polyacrylamide gel electrophoresis was obtained.

EXAMPLE 11

Evaluation of Enzymatic Activity of Enzyme Solution Obtained from Transformed *Aspergillus oryzae*

According to the above-mentioned method for the determination of enzymatic activity, the enzymatic activity (U/mL-b) of GLD in the enzyme solution obtained in Example 10 and the "ratio of activity for xylose/activity for glucose" (Xyl/Glc) were confirmed, and the results were as shown in Table 6. From these results, it is found that a transformant producing a modified GLD having a decreased activity for xylose as compared with the wild-type GLD was obtained.

From the above results, it is found that a modified GLD was obtained by culturing a transformant producing a modified GLD having a decreased activity for xylose as compared with the wild-type GLD.

TABLE 6

| Position of Mutation | GLD Activity (U/mL of a liquid culture medium) | Xyl/ Glc (%) | Ratio of Xyl/Glc (wild-type GLD = 1) |
|---|---|---|---|
| Comparison (Wild-type) | 34 | 8.7 | 1 |
| G73D | 13 | 2.5 | 0.29 |
| R102H | 23 | 4.0 | 0.46 |
| K374Q + P527L | 3.1 | 6.7 | 0.77 |
| G73S | 61 | 3.9 | 0.45 |

EXAMPLE 12

Further, using a culture supernatant of the above-mentioned transformant having the modified GLD gene encoding the modified GLD with a substitution of glycine with aspartic acid at position 73 of the amino acid sequence of the wild-type GLD, the enzyme was purified in accordance with the method described in patent document 2, whereby a purified enzyme showing a single band of about 81 kDa in SDS polyacrylamide gel electrophoresis was obtained.

When the "ratio of activity for xylose/activity for glucose" of this purified modified GLD enzyme was confirmed according to the above-mentioned method for the determination of enzymatic activity, in the case of the wild-type GLD, the ratio was 8.6%, and on the other hand, in the case of the modified GLD with a substitution of glycine with aspartic acid at position 73, the ratio was 4.8%.

Incidentally, in the case of the above-mentioned purified modified GLD, the "ratio of activity for maltose/activity for glucose" was 0.91%, and the "ratio of activity for galactose/activity for glucose" was 0.57%, and therefore, it was revealed that the activity was extremely low.

From the above results, it was confirmed that a modified GLD which did not act on maltose and galactose and had a decreased activity for xylose could be obtained by culturing a transformant producing a modified GLD not only having a decreased activity for maltose and galactose, but also having a decreased activity for xylose as compared with a wild-type GLD.

EXAMPLE 13

Determination of D-Glucose Using Modified GLD

The determination of D-glucose was performed by measuring a change in the absorbance using the enzyme solution of the purified enzyme solution (specific activity: 631 U/mg) from the transformant producing the modified GLD with a substitution of glycine with aspartic acid at position 73 obtained in Example 12. In a reaction measurement system using a plate reader, D-glucose was added such that the final concentration of D-glucose became 0.3, 1.0, 5.0, 10, or 33 mM, and a change in the absorbance of DCIP at 600 nm (ΔAbs/min) was determined. When the change in the absorbance was plotted against the known glucose concentrations (0.3, 1.0, 5.0, 10, and 33 mM), the results shown in Table 7 were obtained and a calibration curve could be prepared based on these results (FIG. 1). From this, it was shown that glucose could be quantitatively determined using the modified GLD of the invention.

TABLE 7

| glucose concentration (mM) | change in the absorbance of DCIP at 600 nm (ΔmAbs/min) |
|---|---|
| 0 | 3.24 |
| 0.3 | 4.9 |
| 1 | 8.58 |
| 5 | 32.6 |
| 10 | 58.9 |
| 33 | 165 |

EXAMPLE 14

Acquisition of Transformant Having Modified GLD Gene Having Site-Specific Substitution Mutation Introduced Therein: Part 2

In addition to Example 4, in order to introduce a site-specific substitution mutation into a GLD gene, oligonucleotides as shown below were designed and synthesized.

```
Primer DNA (S37V):
                                  (SEQ ID NO: 21)
5' attggaggcggtactgtgggtttggccgtcgca 3'

Primer DNA (S37G):
                                  (SEQ ID NO: 22)
5' attggaggcggtactggcggtttggccgtcgca 3'

Primer DNA (T69I):
                                  (SEQ ID NO: 23)
5' aacaatcccaatgtcatcaacgtggatggctac 3'

Primer DNA (L76F):
                                  (SEQ ID NO: 24)
5' tggatggctacgggttcgcttttgggtctga 3'

Primer DNA (F78L):
                                  (SEQ ID NO: 25)
5' gctacgggcttgctttggggtctgacattga 3'

Primer DNA (R102V):
                                  (SEQ ID NO: 26)
```

-continued

```
5' cttagtcaagtgcttgtcgccggcaaggcccctt 3'
```

Primer DNA (N217S):

(SEQ ID NO: 27)
```
5' aagatgcgcggcttttccttataccoctccacc 3'
```

Primer DNA (P240I):

(SEQ ID NO: 28)
```
5' cgtgcatactactggatctacaagtcccgtccc 3'
```

Primer DNA (P240L):

(SEQ ID NO: 29)
```
5' cgtgcatactactggttgtacaagtcccgtccc 3'
```

Primer DNA (Q407L):

(SEQ ID NO: 30)
```
5' cgtctcttcgaggtcctgtatgaccttattttc 3'
```

Primer DNA (Q407S):

(SEQ ID NO: 31)
```
5' cgtctcttcgaggtctgctatgaccttattttc 3'
```

Primer DNA (Y424S):

(SEQ ID NO: 32)
```
5' cgctgaagtcctgaactcgccgggcagcgcgacgt 3'
```

Primer DNA (A437I):

(SEQ ID NO: 33)
```
5' tttgcagaattctggatcctccttcccttcgct 3'
```

Primer DNA (T530A):

(SEQ ID NO: 34)
```
5' ttccatcccgtcggcgcggctgccatgatgcct 3'
```

EXAMPLE 15

In the same manner as the method described in Example 5, a plasmid into which each substitution mutation was introduced was obtained using the plasmid pCGLD containing the wild-type GLD gene, each of the primer DNAs represented by SEQ ID NOS: 21 to 34 synthesized in Example 14, and a synthetic oligonucleotide complementary to each of the primer DNAs. Transformation was also performed in the same manner as described above, and a transformant having a modified GLD gene encoding each modified GLD with a substitution of a part of the amino acid sequence of the wild-type GLD was obtained.

EXAMPLE 16

Evaluation of Enzymatic Activity of GLD in Transformant Having Modified GLD Gene Having Site-Specific Substitution Mutation Introduced Therein: Part 3

The transformants obtained in Example 15 were cultured in the same manner as the procedure described in Example 3 using a medium prepared by subjecting a medium (adjusted to a pH of 7.0 with NaOH) containing 4% (w/v) tryptone (manufactured by BD), 2% (w/v) yeast extract (manufactured by BD), 4% (w/v) glycerin (manufactured by Nacalai Tesque), and water to an autoclave treatment at 121° C. for 15 minutes in place of the TB medium, and the enzymatic activity of GLD in each of the cell-free extracts was determined and evaluated. Mutant strains in which the enzymatic activity (U/mL-b) of GLD per mL of the culture broth in the case where D-glucose was used as a substrate was maintained to a level of one-tenth or more of that of the wild-type strain GLD and the ratio of activity for xylose/activity for glucose (Xyl/Glc) dominantly decreased as compared with that of the wild-type strain were selected and subjected to a genetic analysis. The results are shown in Table 8.

TABLE 8

| No. | Oligonucleotide Primer No. | Position of Amino Acid Mutation | GLD Activity (U/mL-b) | Xyl/Glc (%) | Ratio of Xyl/Glc (wild-type GLD = 1) |
|---|---|---|---|---|---|
| wt | Non Mutation | Non Mutation | 3.3 | 12.1 | 1 |
| S33 | 21 | S37V | 1.1 | 9.8 | 0.81 |
| S34 | 22 | S37G | 11.5 | 6.9 | 0.57 |
| S35 | 23 | T69I | 2.7 | 8.6 | 0.71 |
| S36 | 24 | L76F | 1.7 | 10.1 | 0.84 |
| S37 | 25 | F78L | 8.6 | 8.7 | 0.72 |
| S38 | 26 | R102V | 1.1 | 9.1 | 0.75 |
| S39 | 27 | N217S | 8.1 | 6.6 | 0.55 |
| S40 | 28 | P240I | 1.5 | 10.3 | 0.85 |
| S41 | 29 | P240L | 1.3 | 9.8 | 0.81 |
| S42 | 30 | Q407A | 2.3 | 6.2 | 0.52 |
| S43 | 31 | Q407S | 2.6 | 6.4 | 0.53 |
| S44 | 32 | Y424S | 1.7 | 10.3 | 0.85 |
| S45 | 33 | A437I | 4.1 | 5.7 | 0.47 |
| S46 | 34 | T530A | 3.4 | 7.2 | 0.59 |

INDUSTRIAL APPLICABILITY

A modified GLD encoded by a polynucleotide of the invention does not substantially act on maltose and galactose in the determination of blood glucose and has a decreased activity for xylose as compared with a wild-type GLD, and therefore can be utilized also in a self-monitoring of blood glucose (SMBG) device with higher accuracy, and largely contributes to self-care and self-treatment by patients with diabetes.

The invention claimed is:

1. An isolated modified glucose dehydrogenase (GLD), comprising an amino acid sequence of a wild-type FAD-conjugated glucose dehydrogenase (GLD) represented by SEQ ID NO: 1 having a substitution of at least one amino acid residue selected from the group consisting of D72A, G73D, G73A, G73S, G73C, G73Q, G73W, G73Y, G73E, G73H, R102H, Y228H, V356A, P527L, S37V, S37G, T69I, L76F, F78L, R102V, N217S, P240I, P240L, Q407A, Q407S, Y424S, A437I, and T530A, wherein a value of a ratio of [activity for xylose]/[activity for glucose] for the isolated modified GLD is 0.85 times or less than a value of a ratio of [activity for xylose]/[activity for glucose] of the wild-type FAD-conjugated GLD.

2. An isolated modified glucose dehydrogenase (GLD), comprising an amino acid sequence of a wild-type FAD-conjugated glucose dehydrogenase (GLD) represented by SEQ ID NO: 1 having an amino acid substitution selected from the group consisting of N64D+R102H+L250Q, G73D, Y228H+A589T, K374Q+P527L, V356A, D72A+G210S, G73A, P527L, D72A, Y228H, G73C, G73H, R102H, D72A+G73D, G73S, G73Q, G73W, G73Y, G73E, S37V, S37G, T69I, L76F, F78L, R102V, N217S, P240I, P240L, Q407A, Q407S, Y424S, A437I, and T530A, wherein a value of a ratio of [activity for xylose]/[activity for glucose] for the isolated modified GLD is 0.85 times or less than a value of a ratio of [activity for xylose]/[activity for glucose] for the wild-type FAD-conjugated GLD.

3. A polynucleotide encoding the isolated modified GLD according to claim 1.

4. The polynucleotide according to claim 3, wherein the polynucleotide encoding the amino acid sequence of the wild-type FAD-conjugated GLD has a base sequence represented by SEQ ID NO: 2.

5. A recombinant vector, comprising the polynucleotide according to claim 3.

6. A transformed cell, which comprises the recombinant vector according to claim 5.

7. The transformed cell according to claim 6, which is *Escherichia coli* or *Aspergillus oryzae*.

8. A method for the production of a modified GLD, comprising: culturing the transformed cell according to claim 6; and collecting a modified GLD from the resulting culture.

9. A method for the determination of glucose, comprising contacting a glucose sample with the isolated modified GLD according to claim 1.

10. A reagent composition for detecting glucose, comprising the isolated modified GLD according to claim 1.

11. A biosensor for detecting glucose, comprising the modified GLD according to claim 1.

12. An isolated polynucleotide encoding the isolated modified GLD according to claim 2.

13. The polynucleotide according to claim 12, wherein the polynucleotide encoding the amino acid sequence of the wild-type FAD-conjugated GLD has a base sequence represented by SEQ ID NO: 2.

14. A recombinant vector, comprising the polynucleotide according to claim 12.

15. A transformed cell, comprising the recombinant vector according to claim 14.

16. The transformed cell according to claim 15, which is *Escherichia coli* or *Aspergillus oryzae*.

17. A method for the production of a modified GLD, comprising: culturing the transformed cell according to claim 15; and collecting a modified GLD from the resulting culture.

18. A method for the determination of glucose, comprising contacting a glucose sample with a modified GLD obtained by the production method according to claim 17.

19. A reagent composition for detecting glucose, comprising the modified GLD obtained by the production method according to claim 17.

20. A biosensor for detecting glucose, comprising the modified GLD obtained by the production method according to claim 17.

21. An isolated modified glucose dehydrogenase (GLD), comprising an amino acid sequence of a wild-type FAD-conjugated glucose dehydrogenase (GLD) represented by SEQ ID NO: 1 having a substitution of at least one amino acid residue selected from the group consisting of D72A, G73D, G73A, G73S, G73C, G73Q, G73W, G73Y, G73E, G73H, R102H, Y228H, V356A, P527L, S37V, S37G, T69I, L76F, F78L, R102V, N217S, P240I, P240L, Q407A, Q407S, Y424S, A437I, and T530A; wherein:

one to four amino acid residues in addition to the amino acid substitution above are substituted, deleted, or added in the amino acid sequence represented by SEQ ID NO: 1, and a value of a ratio of [activity for xylose]/[activity for glucose] for the isolated modified GLD is 0.85 times or less than a value of a ratio of [activity for xylose]/[activity for glucose] for the wild-type FAD-conjugated GLD.

22. An isolated modified glucose dehydrogenase (GLD), comprising an amino acid sequence of a wild-type FAD-conjugated glucose dehydrogenase (GLD) represented by SEQ ID NO: 1 having at least one amino acid substitution selected from the group consisting of N64D+R102H+L250Q, G73D, Y228H+A589T, K374Q+P527L, V356A, D72A+G210S, G73A, P527L, D72A, Y228H, G73C, G73H, R102H, D72A+G73D, G73S, G73Q, G73W, G73Y, G73E, S37V, S37G, T69I, L76F, F78L, R102V, N217S, P240I, P240L, Q407A, Q407S, Y424S, A437I, and T530A in an amino acid sequence of a wild-type FAD-conjugated glucose dehydrogenase (GLD) represented by SEQ ID NO: 1; wherein:

one to four amino acid residues in addition to the amino acid substitution above are further substituted, deleted, or added in the amino acid sequence represented by SEQ ID NO: 1, and a value of a ratio of [activity for xylose]/[activity for glucose] for the isolated modified GLD is less than a value of a ratio of [activity for xylose]/[activity for glucose] for the wild-type FAD-conjugated GLD.

\* \* \* \* \*